United States Patent [19]

Scott et al.

[11] Patent Number: 4,664,521

[45] Date of Patent: May 12, 1987

[54] BIRDSWING DEFECT DETECTION FOR GLASS CONTAINERS

[75] Inventors: Paul F. Scott, Granby, Conn.; Dale J. Brady, Orange Park, Fla.

[73] Assignee: Emhart Industries, Inc., Farmington, Conn.

[21] Appl. No.: 707,267

[22] Filed: Mar. 1, 1985

[51] Int. Cl.⁴ .......................................... G01N 21/90
[52] U.S. Cl. ................................ 356/240; 209/526; 250/223 B; 356/428
[58] Field of Search ................. 356/239, 240, 428; 250/223 B; 209/524, 526

[56] References Cited

U.S. PATENT DOCUMENTS

| | | | |
|---|---|---|---|
| 3,629,595 | 12/1971 | Des Peres | 250/223 B |
| 3,811,567 | 5/1974 | Tomita et al. | 209/524 X |
| 3,932,042 | 1/1976 | Faani et al. | 356/240 |
| 4,249,075 | 2/1981 | Lovalenti | 356/240 X |
| 4,487,322 | 12/1984 | Juvinall | 356/240 X |

FOREIGN PATENT DOCUMENTS

| | | |
|---|---|---|
| 2834587 | 3/1979 | Fed. Rep. of Germany . |
| 2909061 | 9/1980 | Fed. Rep. of Germany . |
| 3245908 | 6/1984 | Fed. Rep. of Germany . |
| 2320549 | 3/1977 | France . |
| 1406392 | 9/1975 | United Kingdom ............... 356/240 |
| 2071641 | 9/1981 | United Kingdom ............... 356/240 |

Primary Examiner—Davis L. Willis
Assistant Examiner—Matthew W. Koren
Attorney, Agent, or Firm—Arthur B. Moore; Arthur J. Samodovitz

[57] ABSTRACT

Method and apparatus for detecting "birdswing" flaws in glass containers. A container is illuminated using a beam of light introduced at its base. The column of light passes up through the container along its inner sidewall until it impinges upon a birdswing or like defect at the inner wall, which will cause light rays to be reflected through the outer wall. The light rays advantageously illuminate a zone at the base of the bottle which does not extend beyond the outer side wall, and are evenly distributed over a defined range of incident angles. Light reflected through the outer sidewall is detected as a bright spot by a suitable photodetector array, which monitors the entire container sidewall. This inspection technique effectively eliminates undesired indications of defects within the container wall, as well as of patterns embossed on the outer surface.

17 Claims, 5 Drawing Figures

BIRDSWING DEFECT DETECTION FOR GLASS CONTAINERS

BACKGROUND OF THE INVENTION

The present invention relates to inspecting glass containers and other containers having transparent or translucent sidewalls, and more particularly to inspecting such containers for forming defects such as "birdswings".

A variety of types of defects are known to occur in glass containers as a result of the forming process. The method and apparatus of the present invention are particulary applicable to the detection of structural irregularities on the inner surface of the container sidewalls. One such defect, known as a "birdswing", is formed when the two sides of the container contact each other during the formation of the parison and prior to blowing the container into its final shape. At this stage the touching of the two walls of the container may cause the hot glass sides to fuse together, so that as the container is blown to its final shape the sides which have touched will move away from each other forming a small thread of glass therebetween, i.e. a "birdswing". A birdswing need not comprise a complete thread between the two inner walls, inasmuch as the thin filament of glass may break rather than stretch during rapid cooling of the article. Inevitably, however, there will be a small conical protruberance from the sidewall directed toward the opposite sidewall.

Various prior art practitioners have sought to detect birdswings and other defects by passing a light beam through the wall of the container. Illustrative patents of this type include U.S. Pat. No. 4,438,492, to W. R. Albers; U.S. Pat. No. 3,662,883, to J. R. Sager; and a series of patents commonly assigned to Inex, Inc. including U.S. Pat. No. 3,886,356 to Gomm et al.; U.S. Pat. No. 3,877,821 to Price et al.; U.S. Pat. No. 3,932,767 to Gomm et al.; and U.S. Pat. No. 3,956,629 to Gomm et al. These systems generally use a solid state television camera or similar electro-optical detection device to scan the glass container, which is illuminated from behind. The birdswing appears as a "dark spot" in the image as the filament and its attachment to the sidewall occlude light passing through the container. This approach encounters a number of serious shortcomings in accuracy and sensitivity. Other defects, such as checks, cracks, blisters, or stones might appear in the wall of the container, also causing dark spots in the image. There is a serious risk of these other types of defects being mistaken for birdswings when in some cases only the latter defect is of concern. Thus, if the detection threshold of these devices is set at a sufficiently low value to discover relatively small birdswings, the system may reject acceptable glassware. In addition, lettering or other patterns embossed on the outer surface of the glassware will also appear as dark spots. If these surface decorations are masked in order to prevent detection, any birdswings appearing thereunder will not be detected.

U.S. Pat. No. 4,249,075 to Lovalenti discloses an alternative apparatus for detection of birdswing defects. In the Lovalenti system a container under inspection is rotated and a laser is directed through the opening defined by its finish, toward the container base. If no birdswing is present, the laser beam will pass through the bottom, but the presence of a birdswing being scanned will cause the laser light to be scattered, and detected by a circumferential protocell array. With reference to page 3, lines 8 et. seq. of the Lovalenti specification, this detection system suffers the shortcoming that the user must accept a tradeoff between the sensitivity of this device to relatively small birdswings as against the portion of the inner container wall which will be effectively scanned.

A variety of prior art references apply a further detection principle to the general task of inspecting glassware for various types of defects, in which the ware is scanned to monitor any light reflected by the defect. Illustrative U.S. patents disclosing apparatus of this nature include:

U.S. Pat. No. 3,328,000: Rottmann
U.S. Pat. No. 3,349,906: Calhoun et al.
U.S. Pat. No. 3,415,370: Husome
U.S. Pat. No. 3,529,167: Calhoun
U.S. Pat. No. 3,601,616: Katsumata
U.S. Pat. No. 3,651,937: Kronseder
U.S. Pat. No. 3,834,429: Schulz
U.S. Pat. No. 3,987,301: O'Conner
U.S. Pat. No. 4,002,823: Van Osterhout
U.S. Pat. No. 4,140,901: Fischer et al.
U.S. Pat. No. 4,165,277: Frewin
U.S. Pat. No. 4,171,481: Mima et al.
U.S. Pat. No. 4,213,042: Beach et al.
U.S. Pat. No. 4,221,961: Peyton
U.S. Pat. No. 4,399,357: Dorf
U.S. Pat. No. 4,424,441: Bieringer et al.

None of the above-listed references disclose an inspection system which would be particularly well suited to provide an accurate and sensitive detection of birdswing defects. U.S. Pat. No. 4,165,277 to Frewin describes a monitoring unit having a plurality of scanning photodiodes with associated phototransistors. The photodiodes are sequentially energized to emit light pulses, illuminating an area of interest of the glassware. Error pulses are generated by phototransistors when a defect is sensed in light reflected from the article. The Frewin apparatus, designed for detection of "in the wall" defects, would not effectively descriminate between birdswings and other defects.

U.S. Pat. No. 4,424,441 to Bieringer et al, discloses photoinspection apparatus in which the container finish is illuminated with diffused light in order to monitor the finish for check-type defects having a horizontal component—an approach obviously unsuitable for detection of birdswings. The apparatus of U.S. Pat. No. 4,399,357 to Dorf et al., which is specially designed for detection of defects such as horizontal checks in the sidewall of a glass container, directs radiant energy into the sidewall of the container from above while the container is rotated. The Dorf system trains a detector device such as a television camera on the outer sidewall to scan the container for light reflected by a horizontal check or similar defect within the sidewall. The Dorf et al. apparatus would not provide sensitive and reliable detection of birdswings and similar forming defects on the interior of the container sidewalls, nor avoid undesired detection of other defects. Inasmuch as it relies on light internally transmitted through the sidewall to detect defects, it is highly vulnerable to various transmission losses.

Accordingly, it is a principal object of the present invention to achieve apparatus for detecting birdswings and like forming defects, in a sensitive and reliable fashion. A related object is to detect an appreciably complete percentage of birdswing defects present in the container, while avoiding signals indicative of other defects such as imperfections within the sidewall. Another related object is to avoid undesired indications of embossed surface decorations on the exterior of the container sidewalls.

An additional object of the invention is to achieve container inspection apparatus which effectively scans the entire inner sidewall of glass containers. This object should be satisfied while providing a high sensitivity for detection of relatively small or partially formed birdswings which may appear as spikes.

A further object of the invention is to design apparatus for detection of birdswings which may be effectively used in tandem with inspection apparatus for other types of defects.

Apparatus for this purpose should be sturdy and reliable, and designed to be effectively operated by relatively unskilled users. Most desirably, these inspection devices should have an inspection capability for a variety of container types—e.g. different wall thicknesses, side wall profiles, glass colorations, etc.

SUMMARY OF THE INVENTION

The above and additional objects are satisfied by the method and apparatus of the invention, which provide for the illumination of sidewalls of a glass container or like transparent article with a partially collimated beam of light transmitted through the container's base, while monitoring the container for light reflected through the outer sidewalls by a birdswing or similar forming defect. This technique relies upon a controlled dispersion of light rays which are reflected by birdswings and similar structural imperfections at the container's inner wall, without significant reflections by "within the wall" flaws or by embossed surface decorations.

In a preferred embodiment of the invention, the illuminating column of light is confined within a limited area as it is transmitted through the base, considering a radial cross-section of the container. The light beam preferably illuminates a band at the heel of the bottle which does not extend beyond the outer sidewall, and has an inner edge somewhat beyond the container's inner wall. A column of light thus confined will not cause reflections off exterior features of the container, but will illuminate the inner sidewall in a well defined manner.

Other aspects of the invention pertain to additional optical parameters of the column of light and its constituent rays. Superior results are observed through the use of a partially collimated light beam wherein the rays deviate from a parallel to the container's vertical axis by no more than a limited angle, illustratively between ±15° and ±20°. Most preferably, the rays within this column are substantially evenly dispersed over this range of incident angles. A "fanning out" of rays within the container may assist in detecting abnormally shaped birdswings with unusual root configurations. The wave lengths of light should be maintained within the optical passband of the transparent material.

A further aspect of the invention is the design of suitable apparatus for detecting light rays reflected by a birdswing or similar defect. In the preferred embodiment of the invention, an array of photosensitive elements scan essentially the entire outer sidewall of the bottle. These elements produce characteristic electrical signals in response to the presence of a small region of greater than ambient luminosity. The photodetector apparatus scans the entire sidewall surface by means of circumferentially disposed photosensitive devices or an equivalent optical imaging arrangement, or by rotating the container relative to a video camera or like device trained on the sidewall. A variety of photodetector devices are suitable for this purpose, including, for example, video cameras or a vertical strip of point detectors.

It is a principal advantage of the invention that birdswings and like forming defects will produce brighter than normal spots, whereas typical in-the-wall defects will appear in this detection scheme to be darker than normal. Apparatus embodying the invention may be used in tandem with conventional "back lighting" photoinspection apparatus wherein the former will be sensitive to light spots, and the latter to dark spots, thereby to provide a more comprehensive glass container inspection system.

BRIEF DESCRIPTION OF THE DRAWINGS

The above and additional aspects of the invention are illustrated in the detailed description which follows, taken in conjunction with the drawings in which.

DETAILED DESCRIPTION

Figure 1:
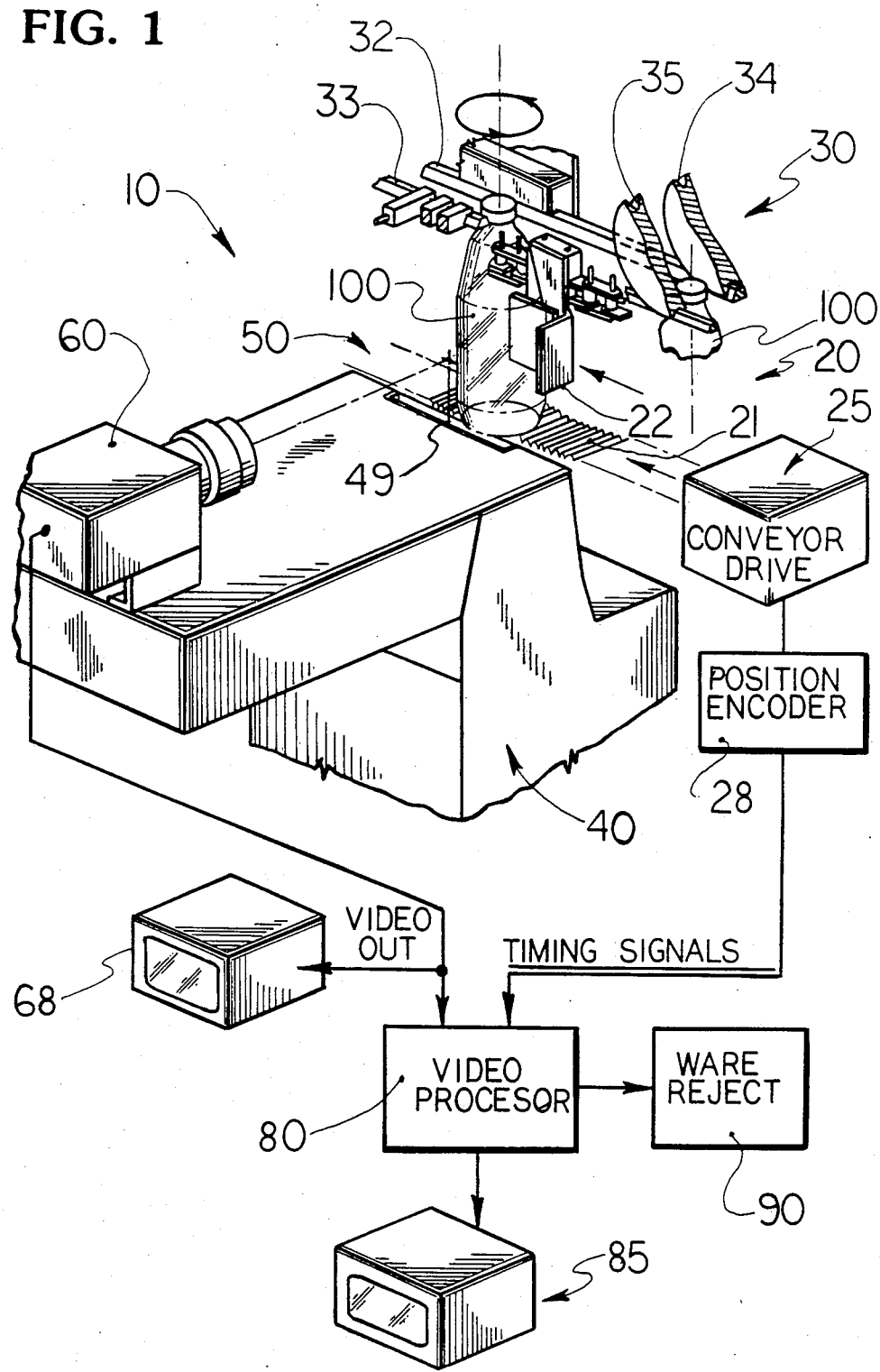
FIG. 1 is a somewhat schematic perspective view of optical inspection apparatus for glassware containers according to the preferred embodiment.

Reference should now be had to FIG. 1, which illustrates somewhat schematically a inspection system for detecting birdswings and like inner-wall defects in glassware articles, according to a preferred embodiment of the invention. Inspection apparatus 10 incorporates an article conveyor 20, including an underlying conveyor 21 and flanged article holders 22, to transport glassware articles 100 past the inspection site 50. In order to provide complete circumferential inspection of the sidewalls of article 100 for inner-wall defects, a pair of resilient belts 32 and 33 nip the article finish to rotate the bottle as shown. The relative speed of belts 32 and 33, respectively driven by pulleys 34 and 35, is chosen to provide a desired number of complete rotations, illustratively on the order of three rotations, as the article passes over the slot 49 of illumination source 40.

As explained in detail below, light directed upwardly from slot 49 through the base of article 100 is selectively reflected by inner-wall forming defects such as birdswings, and may be detected by camera 60 as a bright spot in the scanned image. Image scan data from camera 60 is received as "Video Out" signals by a monitor 68 for direct viewing, and by video processor circuitry 80. Assembly 80 interprets the Video Out signals and recognizes patterns indicative of birdswings or like defects within the scanned portion of article 100. A preferred design of video signal processing apparatus for use in combination with the apparatus of the present invention, utilizing a "bright-streak" processing technique, is disclosed in the commonly assigned application entitled Glassware Inspection Using Optical Streak Detection, in the names of R. Williams and K. P. Westlund. Video Processor 80 receives from Position Encoder 28 indicia of the rate of advance of conveyor 20, and the phase of periodic conveyor operation, via encoded signals from Conveyor Drive 25, and coordinates this information with the Video Out Signals. This optical recognition technique exploits the fact that birdswings and like features will form streaks in a multiframe video image, when scanning a rotating bottle 100. The processed video signals from module 80 may be displayed on monitor 85, or upon recognition of an unacceptable forming defect may actuate Ware Reject Apparatus 90.

It should be understood that the method and apparatus of the present invention relate particularly to the "set-up", i.e. illumination technique, used for inner-wall defect detection, as more fully disclosed below. Secondary aspects include the method of article transport during inspection, the photoinspection apparatus employed, and the means for interpreting the scanned video image. A wide variety of alternatives may be employed for these latter elements of the inspection system. For example, article 100 could be scanned while stationary using a circumferential array of video cameras. Alternative photodetector devices such as a vertical strip of photodiodes are also considered within the scope of the present invention.

It is a principal advantage of our inspection technique that it permits effective detection of birdswing and like inner wall defects over essentially the entire expanse of the article's sidewall. Furthermore, the present apparatus is suitably integrated in a comprehensive defect inspection system, such as one that includes "back-lighting" for detecting in-the-wall defects as dark spots in the scanned image. Advantageously, the sensitivities of the various components of such comprehensive defect systems may be individually adjusted, thus avoiding undesirable tradeoffs found in prior art multipurpose inspection systems. The illumination arrangement described below provides sensitive detection of partially formed birdswings, spikes, and like inner-wall defects while avoiding spurious signals.

Figure 2:
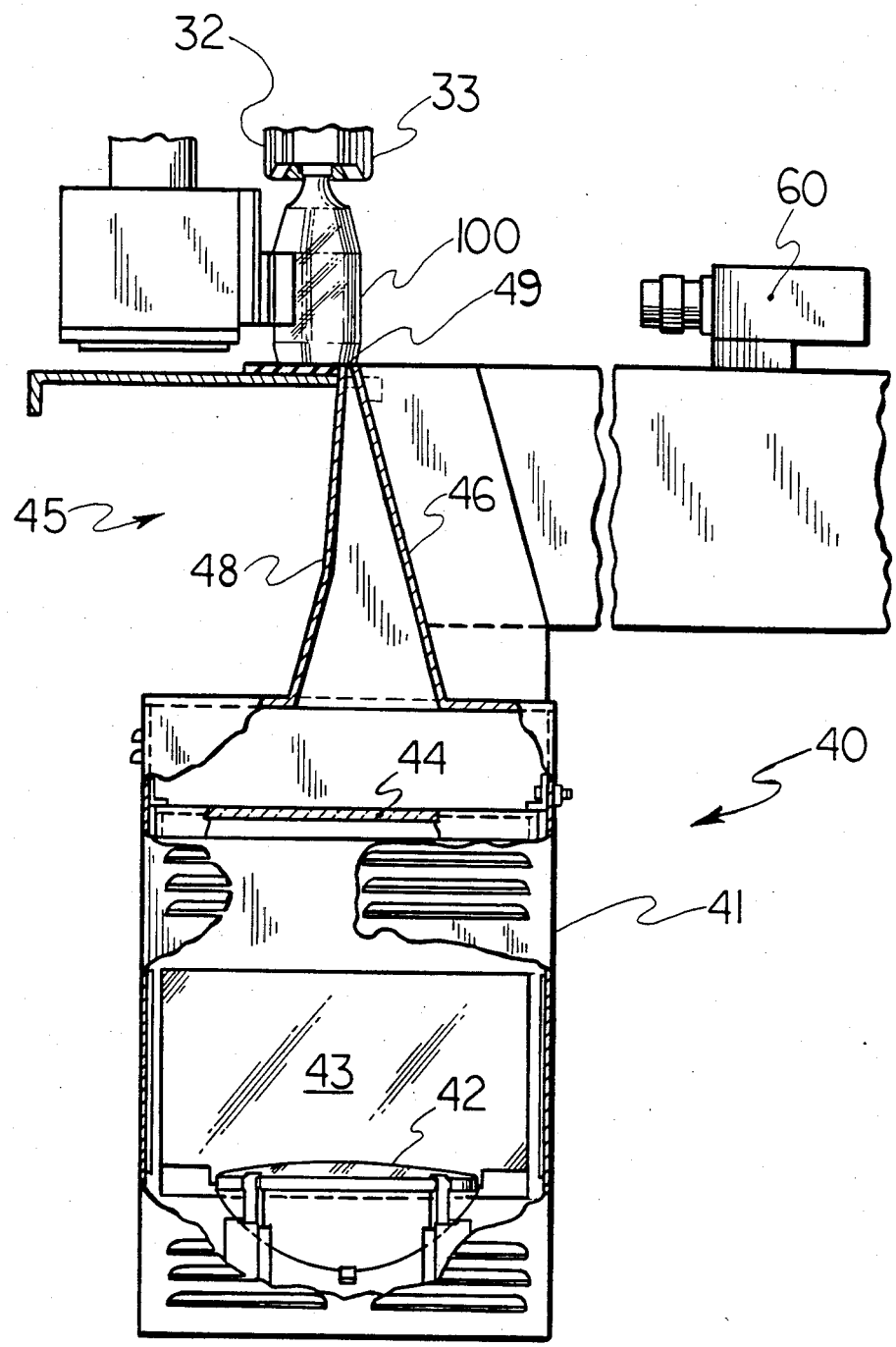
FIG. 2 is a partially cut-away side perspective view of the illumination source assembly of the apparatus of FIG. 1.
Figure 3:
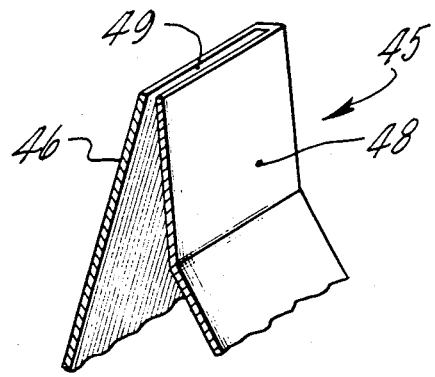
FIG. 3 is an isolated perspective view of the light guide plates from the illumination assembly of FIG. 2.

As best seen in FIG. 2, the illumination source 40 comprises various elements designed to produce an upwardly-directed beam of light through the slot 49, according to defined specifications. Lamp 42 illustratively comprises an incandescent lamp which emits light over spectra within the optical passband of the transparent material of article 100. The walls of cabinet 41 surrounding lamp 42 are lined with mirrors 43 of which one is seen in FIG. 2, to direct uncollimated light through Fresnel lens 44. Light passed by Fresnel lens 44 is received by light guide assembly 45 including converging plates 46, 48, which are lined with a nonreflective material, and create a partially collimated beam of light through slot 49 (see FIG. 3). In accordance with principles of the invention illustrated below, this light output desirably comprises a reasonably even dispersion of light rays over a range of incident angles. The illustrated optics assembly 40 will provide upwardly directed light rays over a range between about 15° from vertical fanning out within bottle 100, and about 5° fanning out in an exterior direction—a dispersion which provides excellent birdswing detection characteristics as explained below. These parameters are determined by the inclination of the light guide plates 46, 48 respectively. Slot 49 is disposed near the outer edge of the heel of bottle 100 as it traverses the slot generally parallel thereto (FIG. 1).

Figure 4:
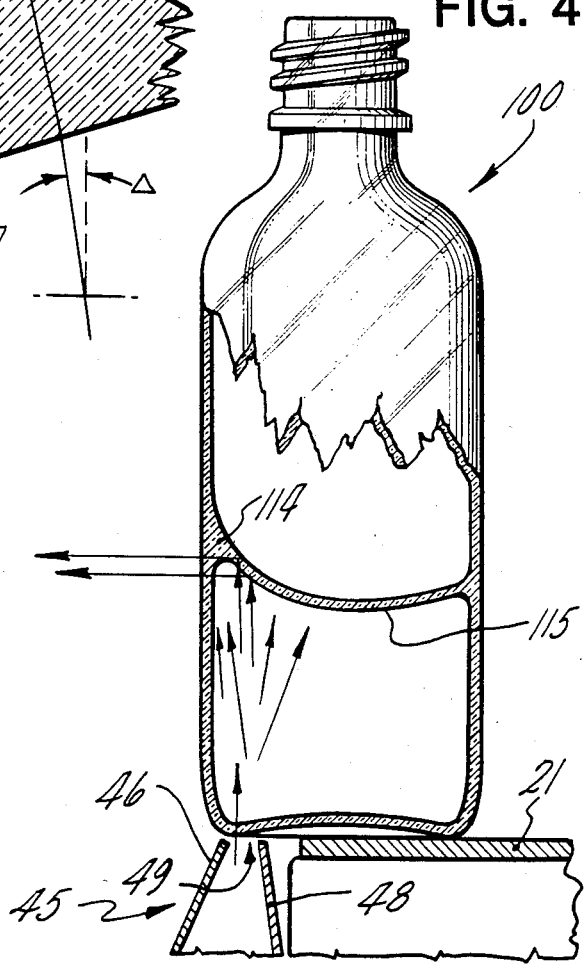
FIG. 4 is a partially sectioned side perspective view of a bottle at the inspection site of the apparatus of FIG. 1.

FIG. 4 shows somewhat schematically a partially cut-away bottle 100 illuminated for birdswing detection at the inspection site 50. Light rays emerging from the light guide assembly 45, in this view represented by arrows, largely pass into the interior of bottle 100 through the glass at the heel of the bottle. It is desireable to position the slot 49 close to the outer edge of the bottle's base, but not beyond this point. A suitable width for slot 49 is on the order of $\frac{1}{4}''-\frac{1}{2}''$, depending on the diameter and wall thickness of bottle 100. These light rays desirably are dispersed over a range of incident angles for reasonably accurate detection of a variety of configurations of birdswings 115.

Figure 5:
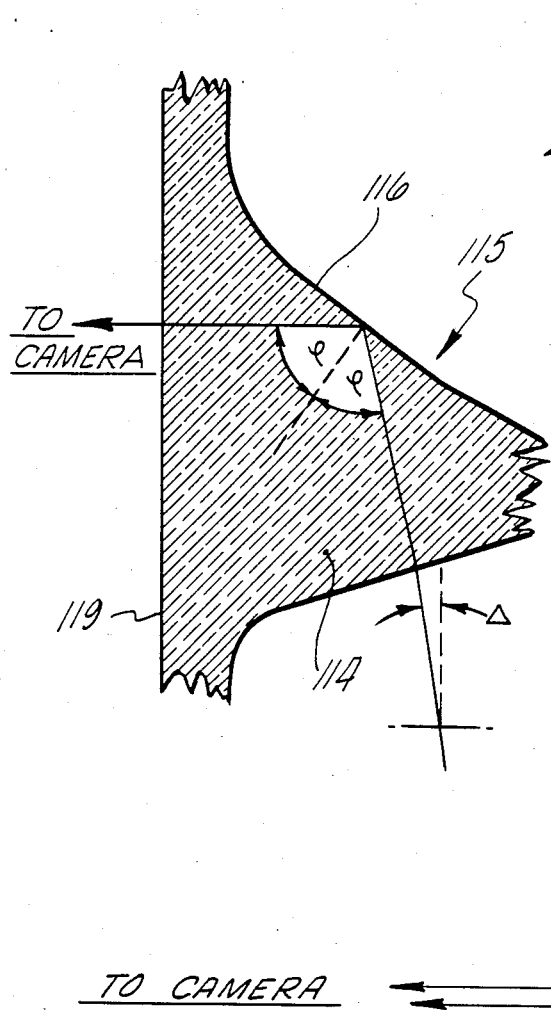
FIG. 5 is a sectional schematic view of a birdswing root transmitting and reflecting a light ray.

As indicated schematically in FIG. 5, this detection techniques relies upon the reflection of light rays off the upper surfaces 116 of birdswings 115, to redirect these rays normally to the outer sidewall 119 of bottle 100, where they will be detected as brighter than the background level by the camera 60. Thus, light directed upwardly at an angle from vertical enters the root 114 of birdswing 115, and reflects off the upper wall 116 provided that the angle of incidence exceeds the critical angle of 41.8 degrees for reflection at a glass-to-air boundary. It should be noted that features such as embossed areas in the outer sidewall 119 will reflect the rays inwardly, and will not create "false positives" in the image scan data. Furthermore, in-the-wall defects such as blisters and stones will not be recognized as inner wall defects.

It has been observed that an even dispersion of light rays upwardly directed into bottle 100 over a range of around ±15° to 20° provides reasonably accurate detection of a variety of inner wall defect configurations. Laser light and collimated light sources are not generally effective for this purpose. The user may adjust the sensitivity of the video scanning and image processing elements to provide a favorable signal to noise ratio, in accordance with the background light level, and the intensity of illumination source 40. This characteristic provides greater flexibility than is found in "back-lighting" systems, in that the latter system's image intensity depends on the opacity of the defects.

While reference has been made above to specific embodiments, it will be apparent to those skilled in the art that various modifications and alterations may be made thereto without departing from the spirit of the present invention. Therefore, it is intended that the scope of this invention be ascertained by reference to the following claims.

We claim:

1. Apparatus for detecting inner-wall defects in transparent articles, comprising:
    means for projecting a partially collimated beam of light upwardly through a base of the article along a side wall of the article at an inspection site;
    means for rotating the article about a central axis of the article at said inspection site, and
    optical detection means placed exterior to the article to detect light emerging from the outer side wall of the article over a given scanning area.

2. Apparatus as defined in claim 1, wherein the partially collimated beam of light comprises a dispersion of light rays over a defined range of directions incident to the article base, said range of angles including a parallel to a central axis of the article.

3. Apparatus as defined in claim 1, wherein the partially collimated beam of light comprises a plurality of rays having wavelengths essentially within the optical passband of the transparent article.

4. Apparatus as defined in claim 1, wherein the means for providing a partially collimated beam of light comprises a lamp, and a pair of optically nonreflective guide plates positioned to receive light of said lamp and converging to form a slot at the article's base, said slot having a width substantially less than the articles diameter, wherein light projected by the lamp is selectively transmitted through said slot to define the beam.

5. Apparatus as defined in claim 4, further comprising means intermediate said lamp and said guide plates for intensifying the light projected through the slot.

6. Apparatus as defined in claim 1, wherein the optical detection means comprises means for detecting bright spots in the scanning area image, means for providing a plurality of chronologically sequential image frames during the scanning interval, and means for recognizing bright streaks in the sequential image frames.

7. Apparatus as defined in claim 1 wherein the beam of light is confined within a zone at the article base extending from a first point near to and inwardly of the article sidewall inwardly to a second point within the article.

8. Apparatus as defined in claim 1, in combination with apparatus for detecting in-the-wall defects by directing light through the article sidewall and scanning the article for darker-than-normal image elements.

9. Apparatus as defined in claim 1, wherein the optical detector means detects light emerging essentially perpendicularly to the article's outer sidewall.

10. Apparatus for detecting inner-wall defects in glassware container and the like, comprising:
    an illumination source assembly, comprising a source of uncollimated light, means for projecting a portion of the uncollimated light through a base of the container along an inner sidewall of said article, and means for limiting said portion within a given area and range of incident angles at the container's base, the given area comprising a band extending between the article sidewall and the interior of said container; and
    an optical detection assembly, for scanning light emerging from a selected area of the container sidewall, and detecting bright spots within a resulting video image.

11. Apparatus as defined in claim 10, wherein the optics assembly further comprises means for increasing the intensity of the portion of uncollimated light prior to limiting thereof.

12. Apparatus as defined in claim 10, wherein the means for limiting said portion comprises a pair of optically nonreflective plates terminating in a slot at the container's base.

13. Apparatus as defined in claim 10, further comprising means for rotating the article about a central axis during a detection interval, and wherein the optical detector assembly comprises a video camera which scans the selected area of the container sidewall during the detection interval.

14. Apparatus for detecting inner-wall defects in glassware container and the like, comprising:
    an illumination source assembly, comprising a source of uncollimated light, means for projecting a portion of the uncollimated light through a base of the container along an inner sidewall of said container, and means for confining said portion within a given area and angular range of plus or minus twenty degrees at the container's base relative to a parallel to a central axis of the container; and
    an optical detection assembly, for scanning light emerging from a selected area of the container sidewall, and detecting bright spots within a resulting video image.

15. Apparatus for detecting inner-wall defects in transparent articles, comprising:
    means for projecting a beam of light upwardly through a base of the article along a side wall of the article at an inspection site, the beam of light being confined within a zone at the articles' base, said zone extending from a first point near to and inwardly of the article sidewall inwardly to a second point within the article, and
    optical detection means placed exterior to the article to detect light emerging from the outer side wall of the article over a given scanning area.

16. Apparatus for detecting inner-wall defects in transparent articles, comprising:
    means for provides a partially collimated beam of light directed through a base of the article along a side wall of the article at an inspection site, the beam of light being confined within a narrow zone at the articles' base, said zone comprising a band extending along the container side wall and essentially oriented along a tangent to the article; and
    optical detection means placed exterior to the article to detect light emerging from the outer side wall of the article over a given scanning area.

17. Apparatus as defined in claim 16, wherein the partially collimated beam of light comprises light rays dispersed over a range of angles at least plus or minus fifteen degrees relative to a vertical axis of the article.

* * * * *